United States Patent [19]

Monte et al.

[11] 4,098,758

[45] Jul. 4, 1978

[54] INORGANIC-ORGANIC COMPOSITES AND METHODS OF REACTING THE SAME WITH ORGANO-TITANIUM COMPOUNDS

[75] Inventors: Salvatore J. Monte, Staten Island; Paul F. Bruins, Douglaston, both of N.Y.

[73] Assignee: Kenrich Petrochemicals, Inc., Bayonne, N.J.

[21] Appl. No.: 694,576

[22] Filed: Jun. 10, 1976

Related U.S. Application Data

[63] Continuation of Ser. No. 556,879, Mar. 10, 1975, abandoned, which is a continuation-in-part of Ser. No. 460,331, Apr. 12, 1974, abandoned.

[51] Int. Cl.$^2$ .................. C04B 31/00; C09C 3/00; C11C 1/00; C08K 9/00
[52] U.S. Cl. .................. 260/42.14; 106/285; 106/288 R; 106/288 Q; 106/290; 106/296; 106/297; 106/299; 106/300; 106/304; 106/305; 106/306; 106/307; 106/308 Q; 106/308 F; 106/309; 260/414; 260/429.5
[58] Field of Search ................ 260/414, 42.14, 429.5; 106/308 Q, 308 F, 299, 300

[56] References Cited

U.S. PATENT DOCUMENTS

| | | | |
|---|---|---|---|
| 2,621,193 | 12/1952 | Langkammerer | 260/414 |
| 3,337,391 | 8/1967 | Clayton et al. | 260/429.5 |
| 3,461,146 | 8/1969 | Turner | 260/414 |
| 3,660,134 | 5/1972 | Morris et al. | 106/308 Q |
| 3,697,474 | 10/1972 | Morris et al. | 260/42.14 |
| 3,697,475 | 10/1972 | Morris et al. | 260/42.14 |
| 3,784,579 | 1/1974 | McGlothlin et al. | 260/414 |

FOREIGN PATENT DOCUMENTS

| | | | |
|---|---|---|---|
| 733,224 | 7/1955 | United Kingdom | 260/429.5 |

*Primary Examiner*—Helen M. McCarthy
*Attorney, Agent, or Firm*—Bert J. Lewen

[57] ABSTRACT

Novel organo-titanates, mixtures thereof, and products thereof and inorganic particulate surfaces and methods of making such reaction products. The reaction, which preferably occurs in an organic medium, modifies the inorganic surface by forming a monomolecular organic complex layer. The modified surface causes complete dispersion and improved compatibility of the inorganic particles or fibers in organic media and results in lower viscosity, high inorganic-to-organic ratios than heretofore obtainable, and improved physical properties in polymer systems, and more complete chemical utilization of reactive inorganic compounds.

12 Claims, No Drawings

INORGANIC-ORGANIC COMPOSITES AND METHODS OF REACTING THE SAME WITH ORGANO-TITANIUM COMPOUNDS

PRIOR APPLICATION

This application is a continuation of co-pending U.S. application Ser. No. 556,879, filed Mar. 10, 1975 which, in turn, was a continuation-in-part of U.S. patent application Ser. No. 460,331, filed Apr. 12, 1974, both now abandoned.

BACKGROUND OF THE INVENTION

Inorganic materials have long been used as fillers, pigments, reinforcements and chemical reactants in polymers. They are essentially hydrophilic, i.e., easily wetted by water or able to adsorb water. However, their compatibility with polymers is limited. Therefore, poor utilization is obtained of the potential reinforcement, of color or opacity, or chemical reactivity of inorganic materials.

For example, zinc oxide is a commonly used component in rubber compounds. When comminuted zinc oxide is added to a rubber compound as a dry powder, it is difficult to disperse it completely in the rubber. On the other hand, predispersion of the zinc oxide in an organic medium which is a plasticizer for the rubber forms a stiff paste which is not dusty, is easy to weigh, and aids in the dispersion in the rubber.

Likewise, other comminuted inorganic solids such as magnesium oxide, calcium oxide, other metal oxides, and fillers such as clay, calcium carbonate, colloidal silica and carbon black may be predispersed in an organic plasticizer or polymer prior to addition to a rubber or plastic compound.

Organo-titanium compounds are well known. A wide variety may be prepared from tetraalkyl ortho titanates by reaction with organic acids.

Organo-titanates having di- or tri- alkyl hydrolyzable groups and with, therefore, only one or two organic groups which are non-hydrolyzable have been used to treat the surfaces of inorganic materials in order to render them hydrophobic, as for example in U.S. Pat. No. 3,660,134. Such di- or tri- alkyl hydrolyzable titanates form a multi-molecular layer or envelope around the inorganic particles, resulting in less efficient use of the organo-titanate, as well as a weaker bond between the inorganic particle surface and the organic continuous phase.

The reaction is accomplished by adding the organo-titanate to a suspension of the inorganic material in an inert solvent such as naphtha, trichloroethylene, toluene or hexane. After the reaction is completed, the solvent is removed and the treated, dried inorganic material is subsequently incorporated in an organic polymer system. U.S. Pat. No. 3,697,475, for example, incorporates such treated inorganic fillers in thermoplastic polymer films.

SUMMARY OF THE INVENTION

The novel organo-titanates of the invention may be represented by the formula:

$$\text{Ti(OR)}_{4-n}(\text{OCOR'})_n$$

where OR is a hydrolyzable group; R' is a non-hydrolyzable group; and n is between about 3.0 and 3.50, preferably from 3.1 to 3.25. The aforesaid compounds are preferred for treating the inorganic solids for reasons hereinafter set forth.

Another composition of matter of the invention is the reaction products of organo-titanates having the above general formula, wherein n is between 3 and 3.5, preferably above 3, and most desirably between 3.1 and 3.25 and inorganic solids. The amount of the organo-titanate compound required is at least 0.1 part, preferably 0.5 to 10 parts, per 100 of the inorganic solid. The reaction takes place on the surface of the inorganic solid, whereby the hydrolyzable group is removed and a bond is established, thus forming an organic, hydrophobic surface layer on the inorganic solid. The inorganic solid, prior to surface modification, is difficult to disperse in an organic medium because of its hydrophilic surface. However, when the organo-titanium compound is incorporated into an organic medium (low molecular weight liquids or higher molecular weight polymeric solids), the surface of the inorganic solid is wet-out, agglomerates are readily broken into individual particles, and a dispersion having improved properties is formed. Alternatively, the organo-titanate may be first reacted with the inorganic solid in the absence of an organic medium and thereafter admixed with the latter.

The method of the present invention converts the surfaces of inorganic materials from a hydrophilic to a hydrophobic state preferably by reaction in an organic medium. This preferred procedure eliminates the prior art intermediate steps of dispersing the inorganic material in a solvent, reacting, filtering and drying the inorganic solid before dispersing it in a polymer.

By means of the present invention, the dispersion of inorganic materials in organic polymer media is improved in order to obtain: (1) lower viscosity or higher loading of the dispersate in the organic medium; (2) higher degrees of reinforcement by the use of fillers, thereby resulting in improved physical properties in the filled polymer; (3) more complete utilization of chemical reactivity, thereby reducing the quantity of inorganic reactive solids required; (4) more efficient use of pigments and opacifiers; (5) higher inorganic-to-organic ratios in a dispersion, and (6) shorter mixing times to achieve dispersion.

Also, according to the invention herein, the reaction with the single hydrolyzabel group of the organo-titanate may be carried out neat or in an organic medium to form a liquid, solid, or paste-like solid dispersion which can be used in the compounding of the final polymeric system. Such dispersions are very stable, i.e., having no tendency to settle, separate, or harden on storage to a non-dispersible state.

Moreover, the invention simplifies the making of inorganic dispersions in organic media by providing a means to eliminate the solvent, to reduce the cost of processing equipment, and to reduce the time and energy required to disperse an inorganic solid material in a liquid or polymeric organic solid.

The objectives of the invention are achieved by the production of a novel liquid ester that simplifies the making of a dispersion in situ.

The present invention results in the formation of a reinforced polymer which has a lower melt viscosity, improved physical properties, and better pigmenting characteristics than are displayed in prior art materials.

The practice of the present invention achieves a product comprising natural or synthetic polymers which contain particulate or fibrous inorganic materials which reinforce, pigment, or chemically react with the polymer to produce a product having superior physical properties, better processing characteristics, and more efficient utilization of pigments.

Amongst the advantages gained by the practice of this embodiment of the present invention is the dispensing with the use of volatile and flammable solvents as required in the prior art. Thus, it is not necessary to dry the filler or to recover solvents. Furthermore, there is no possibility of a multi-molecular layer formation since there is only one hydrolyzable group in the organo-titanate reactant. Also, the practice of the present invention results in a non-oxidizing dispersion.

While many of the compounds of the basic starting material $Ti(OR)_4$ may be used in preparing the polyesters, from the viewpoint of reactivity and economy, tetraisopropyl titanate is preferred. Referring to the above formula, R, which forms part of the hydrolyzable group, may be a straight chain, branched or cyclic alkyl group having from 1 to 5 carbon atoms per molecule. The groups include methyl, ethyl, n- and isopropyl, n-, sec-, and t-butyl, pentyl and cyclopentyl. By "hydrolyzable" is meant a group which will cleave in an aqueous solution having a pH of about 7 at a temperature of less than 100° C. Hydrolysis may be determined by analyzing for liberated acids and alcohols. Conversely, "non-hydrolyzable" means a group that will not hydrolyze under the aforesaid conditions.

With regard to the non-hydrolyzable groups (OCOR'), these are preferably formed from organic acids having 6 to 24 carbon atoms, such as stearic, isostearic, oleic, linoleic, palmitic, lauric and tall oil acids. Isostearic acid is particularly advantageous because it forms a triester that is a liquid at room temperature, which is more readily soluble in organic media. However, the R' group may have from 1 to up to 50 carbon atoms. A major consideration is the total number of carbon atoms in the non-hydrolyzable groups. The sum of the carbon atoms in the three R' groups must be at least 15. Furthermore, at least one R' group must have a long chain, as defined below, in order to give the necessary viscosity reduction to the reaction product of the organic titanate and the inorganic material. As an example, two R' groups may be isopropyl and the long chain R', lauryl. Materials which can be readily liquefied or dissolved at conventional mixing temperatures are most desirable. Equivalent polytitanates may also be used.

Generally, the R' groups have up to 50 carbon atoms, preferably being an alkyl group having up to 24 carbon atoms; an alkenyl group having up to 18 carbon atoms; or an aryl, alkaryl, or aralkyl group having up to 24 carbon atoms. Where the R' group is the long chain group, it must have at least 5 carbon atoms. Additionally, the aforesaid groups may be substituted with halo, nitro, amino, carboxyl, epoxy, or hydroxyl ether or ester groups. Generally from 1 to 6 of such substitutions may occur. Still further, the R' group may contain intermediate hetero-atoms such as oxygen, sulfur or nitrogen in the chain.

All of the R' groups in the organo-titanate compound need not be the same. They may be mixtures of two or more groups, the preparation of which shall be readily understood by those skilled in the art. For example, the $Ti(OR)_4$ starting material may be reacted with two or more organic acids.

The selection of the R' groups for the organo-titanate depends on the particular application. The optimum groups depend on the filler and the monomeric or polymeric organic material, and the desired properties of the filled material. One skilled in the art may determine suitable organo-titanates for specific applications by limited experimental work in light of the teachings herein.

Examples of the R' groups are numerous. These include straight chain, branched chain and cyclic alkyl groups such as hexyl, heptyl, octyl, decyl, dodecyl, tetradecyl, pentadecyl, hexadecyl, octadecyl, nonadecyl, eicosyl, docosyl, tetracosyl, cyclohexyl, cycloheptyl and cyclooctyl. Alkenyl groups include hexenyl, octenyl and dodecenyl.

Groups derived from saturated and unsaturated fatty acids are also useful. In these cases the OCOR' group may be caproyl, caprylyl, capryl, lauryl, myristyl, palmityl, stearyl, arachidyl, behenyl, lignoceryl, dodecylenyl, palmitoleyl, oleyl, ricinoleyl, linoleyl, linolenyl, and gadoleyl.

Halo-substituted groups include bromohexyl, chlorooctadecyl, iodotetradecyl and chlorooctahexenyl. One or more halogen atoms may be present, as for example in difluorohexyl or tetrabromooctyl. Ester-substituted aryl and alkyl groups include 4-carboxyethylcapryl and 3-carboxymethyltoluyl. Amino-substituted groups include aminocaproyl, aminostearyl, aminohexyl, aminolauryl and diaminooctyl.

In addition to the foregoing aliphatic groups, groups containing hetero-atoms, such as oxygen, sulfur or nitrogen, in the chain may also be used. Examples of these radicals are ethers of the alkoxyalkyl type, including methoxyhexyl and ethoxydecyl. Alkylthioalkyl groups include methylthiododecyl groups. Primary, secondary and tertiary amines may also serve as the terminal portion of the hydrophobic group. These include diisopropylamino, methylaminohexyl, and aminodecyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumyl, 1,3,5-triethylphenyl, styryl, allylphenyl, diphenylmethyl, triphenylmethyl, tetraphenylmethyl, 1,3,5-triphenylphenyl. Nitro- and halo-substituted may be exemplified by chloronitrophenyl, chlorodinitrophenyl, dinitrotoluol, and trinitroxylyl.

Amine-substituted components include methylaminotoluyl, trimethylaminophenyl, diethylaminophenyl, aminomethylphenyl, diaminophenyl, ethoxyaminophenyl, chloroaminophenyl, bromoaminophenyl and phenylaminophenyl. Halo-substituted aryl groups include fluoro-, chloro-, bromo-, iodophenyl, chlorotoluyl, bromotoluyl, methoxybromophenyl, dimethylaminobromophenyl, trichlorophenyl, bromochlorophenyl, and bromoiodophenyl.

Groups derived from aromatic carboxylic acids are also useful. These include methylcarboxylphenyl, dimethylaminocarboxyltoluyl, laurylcarboxyltoluyl, nitrocarboxyltoluyl, and aminocarboxylphenyl. Groups derived from substituted alkyl esters and amides of benzoic acid may also be used. These include aminocarboxylphenyl and methoxycarboxyphenyl.

Titanates wherein R' is an epoxy groups include tall oil epoxides (a mixture of 6 to 22 carbon alkyl groups) containing an average of one epoxy group per molecule and glycidol ethers of lauryl or stearyl alcohol.

Substituted naphthyl groups include nitronaphthyl, chloronaphthyl, aminonaphthyl and carboxylnaphthyl groups.

Specific compounds which have been prepared and found operative in the practice of the instant invention include: $(CH_3)_2CHOTi[OCO(CH_2)_{14}CH(CH_3)_2]_2OCOC(CH_3)=CH_2$; $(CH_3)_2CHOTi[OCO(CH_2)_{14}CH(CH_3)_2][OCOC(CH_3)=CH_2]_2$;

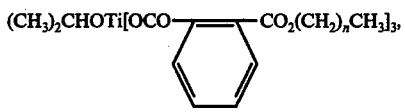

where $n$ is greater than 8 and less than 15;
$[(CH_3)_2CHOTi[OCO(CH_2)_{14}CH(CH_3)_2]_2OCO]_2C_{34}H_{78}$; $(CH_3)_2CHOTi[OCO(CH_2)_{16}CH_3]_3$;

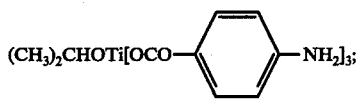

$(CH_3)_2CHOTi[OCO(CH_2)_5NH_2]_3$;
$(CH_3)_2CHOTi[OCOCH_2CH_2NH_2]_3$; and

where the sum of $p + q$ is more than 6 and less than 18.

The inorganic materials may be particulate or fibrous and of any shape or particle size, the surfaces of which are reactive with the hydrolyzable group of the organo-titanium compound by means of hydroxyl groups, or adsorbed water, or both. Examples of inorganic reinforcing materials include metals, clay, carbon black, calcium carbonate, barium, sulfate, silica, mica, glass and asbestos. Reactive inorganic material examples include the metal oxides of zinc, magnesium, lead, and calcium and aluminum, iron fillings and turnings, and sulfur. Examples of inorganic pigments include titanium dioxide, iron oxides, zinc chromate, ultramarine blue. As a practical matter, the particle size of the inorganic material should not be greater than 1 mm, preferably from 1 micron to 500 micron.

It is imperative that the organic titanate be properly admixed with the inorganic material so as to permit the surface of the latter to react sufficiently. The optimum amount of the titanate to be used is dependent on the effect to be achieved, the available surface area of and the bonded water in the inorganic material.

Reaction is facilitated by admixing under the proper conditions. Optimum results depend on the properties of the titanate, namely, whether it is a liquid or solid, and its decomposition and flash point. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate, it may be admixed in any convenient type of intensive mixer, such as a Henschel or Hobart mixer or a Waring blender. Even hand mixing may be employed. The optimum time and temperature is determined so as to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 350° to 450° F.; high density polyethylene from 400° to 475° F.; polystyrene from 450° to 500° F.; and polypropylene from 450° to 550° F. Temperatures for mixing other polymers are known to those skilled in the art and may be determined by reference to existing literature. A variety of mixing equipment may be used, e.g., two-roll mills, Banbury mixers, double concentric screws, counter or corotating twin screws and ZSK type of Werner and Pfaudler and Busse mixers.

When the organic titanate and the inorganic materials are dry-blended, thorough mixing and/or reaction is not readily achieved and the reaction may be substantially completed when the treated filler is admixed with the polymer. In this latter step, the organic titanate may also react with the polymeric material if one or more of the R' groups is reactive with the polymer.

To illustrate further the invention, attention is directed to the following examples:

EXAMPLE A: PREPARATION OF ORGANO-TITANATE ESTERS

One mole of tetraisopropyl titanate is admitted to a vessel equipped with an agitator, an internal heating and cooling means, a vapor condenser, a distillate trap and liquid-solid feed input means. Agitation is commenced with the tetraisopropyl titanate at room temperature. Liquid isostearic acid is metered into the vessel at a controlled rate so that the exothermic reaction is maintained below about 350° F. until 3.19 moles of the acid are added. The isopropanol is removed from the reaction product by distillation at 150° C. at 50 mm Hg to remove potentially objectionable volatiles.

The organic titanate thus produced has an average of 3.19 moles of isostearate per molecule. This material is hereinafter referred to as the "isostearate 3.19 ester." The ester structure is determined by ascertaining the isopropanol liberated from the reaction and the residual isostearic acid. It is found that about from 3.1 to 3.3 moles of isopropanol are recovered in the typical run. Substantially no unreacted isostearic acid is detected. The physical properties of the ester are:

| | |
|---|---|
| Specific Gravity at 74° F. | 0.944 |
| Flash Point (COC), ° F. | 315 |
| Viscosity, LV, at 74° F., cps. | 120 |
| Pour Point, ° F. | Below −5 |
| Decomposition Point, ° F. | Above 400 |
| Gardner Color | 15 Max |
| Appearance | Reddish Oily Liquid |

The above run is repeated, except that instead of adding 3.19 moles of the isostearic acid, 1.0, 2.0 and 3.0 moles are added. This results in the formation of mixtures of isopropyl isostearate titanates having an average number of isostearate groups per molecule of 1, 2 and 3 moles, respectively.

EXAMPLE B

This example demonstrates the effect of admixing the isostearate 3.19 ester with various fillers dispersed in naphthenic oil. The fillers employed include calcium carbonate, calcined clay, high surface area silica, carbon black, and chemically oxidized carbon black. The effect of varying percentages of the titanate ester on the viscosity of the end product is also shown in the data below;

| | Fillers Dispersed in Mineral Oil (Naphthenic Oil) | | | | | | | |
|---|---|---|---|---|---|---|---|---|
| | 1 | 2 | 3 | 4 | 5 | 6 | 7 | 8 |
| $CaCO_3$, parts by wt. | 15 | 35 | 50 | 50 | 70 | 75 | | |
| Mineral Oil, " | 85 | 65 | 50 | 50 | 30 | 25 | | |
| Titanate Ester, % on Filler | — | — | — | 0.5 | 0.5 | 0.5 | | |
| Brookfield Viscosity at 25° C., cps. | 82 | 1,600 | 32,500 | 280 | 2,320 | 12,600 | | |
| Calcined Clay, parts by wt. | 30 | 30 | 50 | 65 | | | | |
| Mineral Oil, " | 70 | 70 | 50 | 35 | | | | |
| Titanate Ester, % on Filler | — | 3 | 3 | 3 | | | | |
| Brookfield Viscosity at 25° C., cps. | 30,000 | 215 | 1,280 | 22,000 | | | | |
| Hi Surface area silica, parts by weight | 5 | 10 | 15 | 20 | 5 | 10 | 15 | 20 |
| Mineral Oil, " | 95 | 90 | 85 | 80 | 95 | 90 | 85 | 80 |
| Titanate Ester, % on Filler | — | — | — | — | 1 | 1 | 1 | 1 |
| Brookfield Viscosity at 25° C., cps. | 120 | 615 | 5,750 | 7,000 | 114 | 520 | 4,700 | 4,100 |
| Hi Surface area silica, parts by weight | 5 | 10 | 15 | 20 | 5 | 10 | 15 | 20 |
| Mineral Oil, " | 95 | 90 | 85 | 80 | 95 | 90 | 85 | 80 |
| Titanate Ester, % on Filler | 2 | 2 | 2 | 2 | 3 | 3 | 3 | 3 |
| Brookfield Viscosity at 25° C., cps. | 92 | 465 | 4,200 | 3,800 | 86 | 345 | 3,000 | 3,500 |
| Commercially Oxidized Carbon Black, pts. by wt. | 10 | 15 | 20 | 25 | 10 | 15 | 20 | 25 |
| Mineral Oil, " | 90 | 85 | 80 | 75 | 90 | 85 | 80 | 75 |
| Titanate Ester, % on Filler | — | — | — | — | 3 | 3 | 3 | 3 |
| Brookfield Viscosity at 25° C., cps. | 462 | 1,612 | 5,000 | 16,800 | 350 | 1,125 | 3,300 | 7,700 |

A regular grade of carbon black was chemically oxidized *in situ* to convert carboxyl groups to hydroxyl groups. The results are shown below:

| Type of Treatment | Brookfield Viscosity at 77° F., cps. of Dispersion |
|---|---|
| Carbon Black (untreated) | 9,200 |
| Carbon Black (5% chemically oxidized) | 15,800 |
| Carbon Black (5% chemically oxidized and treated with 3% titanate ester) | 2,700 |

The aforesaid data clearly show that materials reacted in situ with the titanate ester make dispersions having substantially reduced Brookfield viscosities. Marked reductions in viscosity are shown particularly with the calcium carbonate, calcined clay, and carbon black. This reduced viscosity greatly enhances the ease of mixing these fillers with organic-type materials and results in improved dispersion at lower energy requirements for mixing.

The effect of isostearic isopropyl titanates on the dispersion and chemical reactivity of zinc oxide is shown in the following examples:

EXAMPLE 1: EFFECT OF ISOSTEARATE ESTERS ON THE DISPERSION OF ZINC OXIDE IN AN ORGANIC MEDIUM

| Formulation | Parts by Weight |
|---|---|
| Zinc oxide (−325 mesh, S.A. 5.3 $m^2$/gm.) | 90 |
| Hydrocarbon oil (Naphthenic process oil) | 7 |
| Ester as shown below | 3 |

PENETRATION (ASTM TEST NO. D1231) AT 74° F.

| | Isostearate Esters | | | | |
|---|---|---|---|---|---|
| Days after Mixing | 1.0 mol. | 2.0 mols. | 3.0 mols. | 3.19 mols.* | 3.70 mols. |
| 0 | (Could not make dispersion) | 160 | 170 | 165 | 615 |
| 2 | | 125 | 140 | 150 | — |
| 4 | | 89 | 105 | 118 | — |
| 6 | " | 85 | 105 | 115 | — |
| 7 | " | 80 | 90 | 112 | — |

*The "isostearate 3.19 ester"

The greater the degree of penetration, the more fluid is the mix. After aging, the isostearate 3.19 ester gives the most desirable penetration characteristics. It can be seen by the data that, desirably, the most stable fluid mix is obtained with three or slightly more mols of isostearate in the titanate ester.

The dispersion made with the isostearate 3.19 ester was compared with the same zinc oxide in the untreated powder form in a natural rubber compound except that 10% less zinc oxide was used when making the rubber compound with the treated zinc oxide dispersion described in Example 1. The formulation and test results are shown in Example 2, as follows:

EXAMPLE 2: EFFECT OF TREATED ZINC OXIDE DISPERSION IN A NATURAL RUBBER COMPOUND

FORMULATION

|  | Zinc Oxide Powder (pts. by weight) | 90% Zinc Oxide Dispersion (Example 1) |
|---|---|---|
| Natural Rubber | 100 | 100 |
| Peptizer—REOGEN | 2 | 2 |
| Stearic Acid | 2.5 | 2.5 |
| Zinc Oxide Powder | 3.5 | — |
| 90% Zinc Oxide Dispersion (iso-stearate 3.19 ester) | — | 3.5 |
| HAF Black (N330) | 45 | 45 |
| Sulfur | 2.5 | 2.5 |
| Ultra-Accelerator (AMAX No. 1) | .5 | .5 |

PHYSICAL PROPERTIES

Stress PSI at 300% Elongation (S), Tensile Strength PSI (T), % Elongation (E), Hardness, Shore A (H).

| Press Cures at 290° F. | S | T | E | H | S | T | E | H |
|---|---|---|---|---|---|---|---|---|
| 15 min. | 1120 | 2850 | 500 | 55 | 1380 | 3810 | 550 | 57 |
| 45 min. | 1380 | 2890 | 460 | 59 | 1640 | 3780 | 520 | 59 |
| 60 min. | 1460 | 2900 | 460 | 59 | 1520 | 3610 | 500 | 60 |

RATE AND STATE OF CURE

Rheometer at 290° F., 60 Sec. Preheat, 60 Min. Motor, 100 Range, 3° Arc

|  | Zinc Oxide Powder (pts. by weight) | 90% Zinc Oxide Dispersion (Example 1) |
|---|---|---|
| Max. Torque | 56.2 in./lbs. | 77 in./lbs. |
| Min. Torque | 15 " | 22.5 " |
| T90 (% degree of cure) | 19.5 minutes | 17.5 minutes |
| T95 " | 24 " | 22 " |
| T2 " | 2.2 " | 2.7 " |

PROCESS TIME
Mooney Scorch at 250° F.

|  | Minutes 5 | Minutes 5 |
|---|---|---|
| Time Scorch Begins |  |  |
| Time to 5 Point Rise | 3 | 3 |
| Total Time | 8 | 8 |
| Rise Last Minute | 3 | 3.5 |
| Plasticity | 16 | 35 |

The table in Example 2 shows the great improvement in physical properties of a natural rubber compound achieved by the use of the isostearate 3.19 treatment of the zinc oxide surface even when 10% less zinc oxide is used. Tensile strength is increased by 30%, elongation by 10%, stress at 300% elongation by 10%. It is significant that hardness is not affected. The Mooney plasticity is more than doubled at 250° F., while the rheometer data at 290° F. shows that the treated zinc oxide provides a tighter cure.

The following Example 3 shows the improvement in properties obtained when using the zinc oxide dispersion made with the isostearate 3.19 ester of Example 1 in an oil-black extended SBR (styrene-butadiene rubber) compound:

EXAMPLE 3: EFFECT OF TREATED ZINC OXIDE DISPERSION IN A STYRENE-BUTADIENE RUBBER COMPOUND

FORMULATION

| Compound SBR, Oil-Black Extended | Zinc Oxide Powder (pts. by weight) | 90% Zinc Oxide Dispersion (Example 1) |
|---|---|---|
| PP 1849 (Phillips Petroleum SBR) | 245 | 245 |
| Zinc Oxide | 3 | — |
| 90% Zinc Oxide Dispersion (iso-stearate 3.19 ester) | — | 3 |
| Anti-Oxidant (Flexzone 3C) | 1 | 1 |
| Accelerator-CBTS | 1.3 | 1.3 |
| Sulfur | 2.1 | 2.1 |
| Accelerator-TMTM | 0.55 | 0.55 |
| Ultra-Accelerator (Vultac #5) | 1.2 | 1.2 |
| Resin Modifier Nebony 100 | 10 | 10 |
| Stearic Acid | 1 | 1 |

PHYSICAL PROPERTIES

Stress PSI at 300% Elongation (S), Tensile Strength PSI (T), % Elongation (E), Hardness, Shore A (H).

|  | Zinc Oxide Powder (pts. by weight) | | | | 90% Zinc Oxide Dispersion (Example 1) | | | |
|---|---|---|---|---|---|---|---|---|
| Press Cures at 307° F. | S | T | E | H | S | T | E | H |
| 30 min. | 1175 | 2775 | 600 | 59 | 1325 | 2929 | 580 | 59 |
| Press Cures at 280° F. |  |  |  |  |  |  |  |  |
| 40 min. | 1240 | 2800 | 580 | 60 | 1350 | 2700 | 530 | 61 |

RATE AND STATE OF CURE

Rheometer at 280° F., 60 Sec. Preheat, 60 Min. Motor, 50 Range, 1° Arc

| Max. Torque | 25.75 in./lbs. | 25.75 in./lbs. |
|---|---|---|
| Min. Torque | 5.75 " | 5.65 " |
| TS-2 | 9.5 minutes | 8.25 minutes |
| TC-90 | 22.5 " | 21.75 " |

Rheometer at 340° F., 60 Sec. Preheat, 12 Min. Motor, 50 Range, 1° Arc

| Max. Torque | 21.1 in./lbs. | 22.8 in./lbs. |
|---|---|---|
| Min. Torque | 5.4 " | 5.1 " |
| TS-2 | 2.15 minutes | 1.9 minutes |
| TS-90 | 3.9 " | 3.7 " |

PROCESS TIME
Mooney Data at 212° F.

| Initial | 50.5 | 51.5 |
|---|---|---|
| 1.5 minutes | 40.5 | 41.5 |
| 4.0 minutes | 36.5 | 37.5 |

The data in Example 3 show an equal or improved condition of physical properties with the use of 10% less of zinc oxide. In actual processing, it has been observed that the isostearate 3.19 ester treated zinc oxide dispersion of Example 1 is incorporated into the rubber compound in about one-fourth to one-fifth of the time otherwise required for untreated zinc oxide powder. Additionally, the treated zinc oxide powder was non-dusty.

The above data also show that the compound which contains the treated zinc oxide dispersion has a higher degree of reactivity as well as a tighter final cure, as evidenced by the increase in torque, as compared to the untreated zinc oxide.

The following Examples 4, 5 and 6 illustrate the effectiveness of isostearate 3.19 ester in reducing the viscosity of dispersions of various inorganic solids in a hydrocarbon oil.

The dispersion of zinc oxide in a hydrocarbon oil results in a greatly reduced viscosity when it is reacted with isostearate 3.19 ester, as can be seen in the following Example 4:

EXAMPLE 4

|  | Parts by Weight | |
| --- | --- | --- |
| Zinc Oxide | 50 | 50 |
| Naphthenic Process Oil | 50 | 47.5 |
| Isostearate 3.19 ester | 0 | 2.5 |
| Brookfield Viscosity at 74° F. cps (centipoises) | 460,000 | 80,000 |

The reduction in viscosity of the zinc oxide dispersion in a hydrocarbon oil by the in situ reaction with the isostearate 3.19 ester was 83%.

The viscosity of a dispersion of titanium oxide is similarly reduced by the isostearate 3.19 ester, as shown in the following Example 5:

EXAMPLE 5

|  | Parts by Weight | |
| --- | --- | --- |
| Titanium Dioxide | 50 | 50 |
| Naphthenic Process Oil | 50 | 47.5 |
| Isostearate 3.19 Ester | 0 | 2.5 |
| Brookfield Viscosity at 74° F. cps. | 110,000 | 900 |

The reduction in viscosity of the titanium dioxide dispersion in hydrocarbon oil by the in situ reaction with the isostearate 3.19 ester was 99%.

The viscosity of a dispersion of carbon black in a hydrocarbon oil is similarly reduced by the same ester, as shown in the following Example 6:

EXAMPLE 6

|  | Parts by Weight | |
| --- | --- | --- |
| Carbon Black FEF N550 | 30 | 30 |
| Naphthenic Process Oil | 70 | 65 |
| Isostearate 3.19 Ester | 0 | 3 |
| Brookfield Viscosity at 79° F., cps. | 104,000 | 46,000 |

The reduction in viscosity of the carbon black dispersion in a hydrocarbon oil by the in situ reaction with the isostearate 3.19 ester was 56%.

The viscosity of a dispersion of calcium carbonate in a liquid epoxy resin is reduced when the isostearate 3.19 ester is added, as shown in the following Example 7:

EXAMPLE 7

|  | Parts by Weight | |
| --- | --- | --- |
| Calcium carbonate (low oil absorption type) | 50 | 50 |
| Liquid epoxy resin (epoxide equivalent —185) | 50 | 45 |
| Isostearate 3.19 ester | 0 | 5 |
| Brookfield Viscosity at 74° F., cps. | 550,000 | 110,000 |

The reduction in viscosity of the calcium carbonate dispersion in liquid epoxy resin by the in situ reaction with the isostearate 3.19 ester was 80%.

The viscosity of a dispersion of colloidal silica in a liquid polysulfide rubber is reduced when the isostearate 3.19 ester is added, as shown in the following Example 8:

EXAMPLE 8

|  | Parts by Weight | |
| --- | --- | --- |
| Colloidal silica (Neosil A) | 50 | 50 |
| Liquid polysulfide rubber (Thiokol TP-90B) | 50 | 45 |
| Isostearate 3.19 ester | 0 | 5 |
| Brookfield Viscosity at 74° F., cps. | 8,000 | 2,250 |

The penetration of a paste dispersion of calcium carbonate in a liquid (thiokol) polysulfide rubber was increased when the isostearate 3.19 ester was added. Alternatively, when the amount of calcium carbonate in the dispersion was increased 50%, the penetration remained the same, through the addition of an increased amount of the isostearate 3.19 ester. These effects are shown in the following Example 9:

EXAMPLE 9

|  | Parts by Weight | | |
| --- | --- | --- | --- |
| Calcium carbonate (Purecal SC) | 200 | 200 | 300 |
| Polysulfide liquid rubber (Thiokol LP-32) | 100 | 100 | 100 |
| Isostearate 3.19 ester | 0 | 4 | 15 |
| Penetration (ASTM Test No. D-1321) | 45 | 82 | 46 |

The dispersions of Examples 4 through 9 were initially prepared without the isostearate 3.19 ester by preblending the pigment or filler with the organic liquid medium using a Pony mixer. This preblend was then ground on a three-roll mill to make the final dispersion. Viscosity or penetration measurements were made for a control comparison.

The effect of the titanate ester was then evaluated by a second set of tests in which the titanate ester was added to the organic liquid medium and the dispersion made as described before. Viscosity measurements made on the new batches disclosed very considerable and significant reduction in viscosity demonstrating that the isostearate esters of the invention are effective with a variety of inorganic materials and in different liquid organic media. This reduction in viscosity indicates that inorganic materials treated by the processes disclosed herein can (1) be used in higher loadings, (2) become more completely dispersed in the organic medium and in the end product, and (3) create viscosity levels which lend themselves to improved manufacturing processes such as reduced energy levels for mixing or for pumping of such dispersions.

These examples demonstrate that the inorganic materials do not have to be pretreated and the surface modification can be accomplished in situ by the use of the isostearate titanate ester. Also, the ester is effective in reducing viscosity of a wide variety of inorganic materials in a wide variety of organic media.

The following Example 10 shows the effectiveness of isostearate 3.19 ester in producing a shorter mixing time and lower viscosity in a dispersion of magnesium oxide in hydrocarbon oil. In actual mixing, it is necessary to add the magnesium oxide to the hydrocarbon oil in increments in order to obtain the maximum degree of inorganic to organic loading in the shortest possible tiem. The table below outlines this procedure and the results obtained:

EXAMPLE 10

|  | Parts by Weight |  |
|---|---|---|
| Magnesium Oxide | 55 | 55 |
| Naphthenic Process Oil | 45 | 42 |
| Isostearate 3.19 ester | 0 | 3 |

| Increment Addition No. | Weight | Time in Minutes |  |
|---|---|---|---|
| 1 | 16.67 | 0 | 0 |
| 2 | 8.33 | 0.5 | 0.5 |
| 3 | 8.33 | 1.0 | 1.0 |
| 4 | 8.33 | 2.0 | 2.0 |
| 5 | 5.00 | 4.0 | 2.5 |
| 6 | 4.17 | 4.5 | 3.0 |
| 7 | 4.17 | 5.0 | 3.5 |
|  | 55.00 |  |  |
| Time to Complete Dispersion |  | 6.5 | 4.5 |
| Penetration (ASTM Test No. D-1321) |  | 160 | 230 |

The resultant dispersion was therefore made 30% softer while requiring 31% less mixing time.

EXAMPLE 11

The effect of reacting the isostearate 3.19 ester with calcium carbonate (a precipitated small particle grade) in situ in low density polyethylene (LDPE, sp.g. 0.918) is shown in the table below. This table compares the metl viscosity vs. time in making a dispersion of calcium carbonate in low density polyethylene having a melt index of 7, when 70 parts of calcium carbonate are blended with 28 parts of LDPE.

In these experiments, 2.85% of the isostearate 3.19 ester (based on the calcium carbonate) was added before starting the mixing in a Brabender high intensity mixer. The mixing was carried out at a maximum temperature of 200° F., and at 8 RPM, using a 5 Kg weight on the ram, while the melt viscosity was observed by measuring the torque applied to the mixer in gram meters.

Similar experiments were made when the isostearate ester was omitted, and when two other dispersion aids, namely, aluminum tristearate and polyglycerol 400 mono-oleate, were used at the same concentration, namely, 2.85% (based on CaCO$_3$). The results are also shown in the following table:

| Additives | Torque Readings (gms.-meter$^2$) |  |  |  |  |  |
|---|---|---|---|---|---|---|
|  | Time (seconds) |  |  |  |  |  |
|  | 30 | 60 | 90 | 120 | 150 | 190 |
| Isostearate 3.19 Ester | 1250 | 900 | 900 | 900 | 750 | 750 |
| No Additive | 2000 | 2000 | 1900 | 1750 | 1750 | 1750 |
| Aluminum Tristearate | 1900 | 1400 | 1300 | 1250 | 1250 | 1250 |
| Polyglycerol 400 Mono-Oleate | 2150 | 1400 | 1150 | 1000 | 1000 | 1000 |

When no additive was employed, the torque after 30 seconds of mixing was 2,000 gm.-sq. meter, and after 190 seconds was 1750.

When the isostearate 3.19 ester was used, the torque had dropped to 1250 gm.-sq. meter in 30 seconds, and was 750 at 190 seconds, showing the great reduction in melt viscosity in a very short time.

When the aluminum tristearate was used, the torque had dropped to 1,900 gm-sq. meter after 30 seconds, and to 1,250 after 190 seconds, appreciably higher than the titanate ester. The polyglycerol 400 mono-oleate additive produced a torque of 2,150 gm.-sq. meter after 30 seconds of mixing, and a torque of 1,000 after 190 seconds of mixing.

The effectiveness of the isostearate 3.19 ester as a dispersion agent was also demonstrated by an additional test in which the 70% CaCO$_3$ dispersion was mixed with additional LDPE polymer in the ratio of 1 to 9, and then made into film by blown-film extrusion. The resulting film was then examined visually to measure the number of remaining agglomerated particles per square foot. When no dispersion additive was employed, there were 312 agglomerates per square foot. When the titanate ester was employed, the number of agglomerates dropped to 16 per square foot.

EXAMPLE 12

This example is similar in procedure to that described in Example 11. Titanium dioxide (rutile) was used as the inorganic dispersed phase in the same LDPE as used in Example 11. The dispersion was made at 75 parts TiO$_2$ using 2.67% dispersion additive (based on the TiO$_2$), and 23 parts of LDPE.

The following table shows that with no dispersion additive the torque on the Brabender mixer after 30 seconds was 2,250 gm.-sq. meter, and after 180 seconds had dropped to 1,100. When the isostearate 3.19 ester was added, the torque after 30 seconds was reduced to 1,250 gm.-sq. meter, and after 180 seconds was 750.

| Additive | Torque Readings (gms.-meter$^2$) |  |  |  |  |  |
|---|---|---|---|---|---|---|
|  | Time (seconds) |  |  |  |  |  |
|  | 30 | 60 | 90 | 120 | 150 | 180 |
| Control No Additive | 2250 | 1750 | 1250 | 1250 | 1150 | 1100 |
| Isostearate 3.19 ester | 1250 | 900 | 900 | 900 | 750 | 750 |
| Polyglycerol 400 Mono-Oleate | 2000 | 1500 | 1250 | 1000 | 1000 | 1000 |
| Aluminum Tristearate | 1000 | 750 | 750 | 600 | 500 | 500 |

When the TiO$_2$ dispersion was reduced in concentration to 7.5% and blow film made, the number of agglomerates per square foot without additive was 600, and with the isostearate ester the agglomerate count was reduced to 150 per square foot. There was also a very noticeable increase in opacity and whiteness.

It can also be seen from the table that in the case of TiO$_2$ dispersion the polyglycerol 400 mono-oleate was inferior, while the aluminum stearate was superior to the titanate ester as a dispersion aid.

EXAMPLE 13

This example is similar in procedure to Examples 11 and 12. The inorganic dispersed phase was yellow iron oxide and 50 parts were used with 4% dispersion additive (based on the iron oxide), and 48 parts of LDPE. The following table shows the results.

| Additive | Torque Readings (gms.-meter$^2$) Time (seconds) | | | | | |
|---|---|---|---|---|---|---|
|  | 30 | 60 | 90 | 120 | 150 | 180 |
| Control No Additive | 2500 | 1750 | 1000 | 1000 | 1000 | 1000 |
| Isostearate 3.19 ester | 2500 | 1400 | 850 | 750 | 750 | 750 |
| Aluminum Tristearate | 2000 | 1250 | 850 | 800 | 800 | 800 |
| Polyglycerol 400 Mono-Oleate | 2000 | 1100 | 1000 | 900 | 800 | 800 |

When no dispersion additive was employed, the torque on the Brabender was 2,500 gm.-sq. meter after 30 seconds, and 1,000 after 180 seconds. When the isostearate 3.19 ester was added, the torque after 30 seconds was also 2,500 gm.-sq. meter, but after 180 seconds the torque had dropped to 750.

When the yellow oxide dispersion was reduced to a concentration of 5% and converted into blown film, the agglomerate count was 685 per square foot when no dispersion additive was employed. When the isostearate 3.19 ester was added, the agglomerate count dropped to 113 per square foot.

The above table also shows that the titanate ester was superior to aluminum stearate or polyglycerol 400 mono-oleate in reducing the melt viscosity.

EXAMPLE 14

The isostearate 3.19 titanate ester was used to study the effect of impact, tensile and melt index properties of injection-grade, high density polyethylene (HDPE) with mineral fillers at a loading range of 30–60%.

A laboratory Banbury was used to masterbatch the organic titanate with the HDPE at a concentration of 5%. The resultant compound was ground in a Cumberland grinder employing a 14 mesh screen, and thereafter dry-blended in a Henschel-type mixer with the filler to give the desired filler-to-organic titanate ratio. The dry blend was mixed with more HDPE to give the desired percent filler, using the Banbury in 3 minutes cycle times, 60 psi ram pressure, and a drop temperature of 200° F. The finished compounds were ground and injection-molded into plaques having dimensions of 0.105 × 0.500 × 2.375 inches for testing. The molding took place at 400° F.; at an injection pressure of 1,000 psi; ram forward, 10 seconds; and mold close time of 15 seconds.

The results obtained are shown in the following table:

| Formulation | Filler, percent | Titanate Ester, percent, based on filler | EVA, percent | Melt index, g./10 min. | Tensile Strength, p.s.i. | Tensile Modulus 10$^3$ p.s.i. | Impact Strength ft.-lb./in. of notch |
|---|---|---|---|---|---|---|---|
| Control (HDPE only) | 0 | 0 |  | 19.7 | 2,050 | 98.0 | 0.93 |
| BaSO$_4$ | 30 | 0 |  | 20.8 | 2,430 | 81.7 | 0.58 |
|  | 30 | 3 |  | 22.0 | 2,460 | 49.0 | 0.60 |
|  | 40 | 3 |  | 22.3 | 2,220 | 59.4 | 0.64 |
|  | 50 | 3 |  | 22.3 | 2,060 | 63.3 | 0.76 |
|  | 60 | 3 |  | 22.0 | 1,770 | 70.0 | 0.91 |
| Aluminum Silicate | 30 | 0 |  | 14.0 | 2,510 | 99.8 | 0.40 |
|  | 30 | 3 |  | 12.9 | 3,020 | 133.2 | 0.60 |
|  | 40 | 3 |  | 8.4 | 2,790 | 140.1 | 0.53 |
|  | 50 | 3 |  | 1.5 | 2,490 | 145.3 | 0.45 |
|  | 60 | 3 |  | 0 | 2,350 | 150.9 | 0.37 |
| Calcium Metasilicate, CaSiO$_3$ | 30 | 0 |  | 16.5 | 2,330 | 72.2 | 0.56 |
|  | 30 | 3 |  | 16.5 | 2,230 | 87.2 | 0.77 |
|  | 40 | 3 |  | 16.5 | 2,020 | 106.0 | 0.81 |
|  | 50 | 3 |  | 14.9 | 1,800 | 121.3 | 0.88 |
|  | 60 | 3 |  | 12.0 | 1,610 | 130.8 | 0.93 |
| CaCO$_3$ | 30 | 0 |  | 16.3 | 1,960 | 217.9 | 0.53 |
|  | 30 | 3 |  | 18.8 | 2,330 | 180.6 | 0.57 |
|  | 40 | 3 |  | 18.4 | 1,730 | 163.4 | 0.78 |
|  | 50 | 3 |  | 17.7 | 1,770 | 150.9 | 0.97 |
|  | 60 | 3 |  | 17.8 | 1,800 | 130.8 | 1.01 |
| Ethylene-Vinyl Acetate Polymer with Calcined Clay Filler | 40 | 3 | 5.8 | 2.7 | 2,900 | 112.1 | 0.82 |
|  | 40 | 3 | 10.8 | 2.9 | 2,710 | 109.3 | 1.52 |
|  | 40 | 3 | 15.8 | 5.7 | 2,470 | 106.0 | 2.39 |
|  | 40 | 3 | 20.8 | 7.5 | 2,180 | 102.2 | 4.54 |

The aforesaid table shows that the isostearate 3.19 ester works most effectively with calcium carbonate and barium sulfate. The 30% filler/HDPE system with the organic titanate has better impact strength than the equivalent filled system without the titanate ester. In the case of the 40% filler/HDPE system containing calcium carbonate, calcium metasilicate, and barium sulfate, the impact strength was equal to or better than the high density polyethylene. Additionally, the stiffness or tensile modulus of the calcium carbonate filled HDPE is significantly reduced by 3% of the organic titanate. Surprisingly, it decreases with increased loading. Even though the modulus is reduced significantly, the tensile strength is maintained relatively constant with loadings as high as 60%.

Finally, the melt index of the barium sulfate-or calcium carbonate-filled HDPE remains reasonably constant. At 60% loading, they have flow characteristics similar to the 100% HDPE with no filler.

EXAMPLE 15

In this example the application of the invention to filled low density polyethylene is described. The unfilled polyethylene admixed with 40% calcium carbonate is tested for volume resistivity (V.R.), tensile strength, modulus, elongation and tear strength, as compared to the polyethylene filled with calcium carbonate after having been dry-blended with 1%, 2% and 3% of the isostearate 3.19 ester of the invention as a coupling agent. The results are shown in the following table:

| Properties | Unfilled Polyethylene | 40% Calcium Carbonate | | | |
|---|---|---|---|---|---|
| Percent Isostearate 3.19 Ester | — | 0% | 1% | 2% | 3% |
| V.R., 50° C. ohm-cm × 10$^{14}$ | 60+ | 60+ | 60+ | 60+ | 60+ |
| Tensile Strength, psi | 1638 | 1464 | 1245 | 1222 | 1124 |
| 300% Modulus, psi | 1204 | — | — | — | 964 |
| Elongation | 530 | 40 | 80 | 150 | 420 |
| Tear Strength, Die C: Pounds per inch | 500 | 228 | 262 | 276 | 284 |
| Relative energy to tear | 1100 | 100 | 230 | 280 | 450 |

It will be noted that the treatment with the organo-titanate improves the elongation and the tear strength as compared to the untreated filled material. However, it should be noted that these properties are not restored to the level of the unfilled polyethylene.

EXAMPLE 16

This example shows the effect of the isostearate 3.19 ester dry-blended with calcium carbonate on the impact strength of filled polypropylene. In these experiments, the heat-aged and unaged impact strengths are compared for unfilled polypropylene, polypropylene filled with 40 weight percent calcium carbonate, and polypropylene filled with 40 weight percent calcium carbonate which had been previously dry-blended with the amounts of the isostearate 3.19 ester (based on CaCO$_3$) as shown in the table below. Heat aging at 150° C. is an accelerated test of the long term aging effects at ambient temperatures. The dry blending was done with a high intensity Henschel type mixer at ambient temperature for a period of at least 30 sec. at 3600 rpm.

The following table shows the impact strength of the unaged and heat-aged samples:

| Composition | Unnotched Izod Impact Strength ft. lb./in. width | |
|---|---|---|
| | Unaged | Heat Aged at 150° C. for 48 hours. |
| Unfilled Polypropylene | 8.3 | Not tested |
| Polypropylene containing 40% calcium carbonate | 6.3 | 0.57 |
| Polypropylene containing 40% calcium carbonate dry-blended with 0.5% isostearate 3.19 ester | 5.9 | 6.0 |
| Polypropylene containing 40% calcium carbonate dry-blended with 0.75% isostearate 3.19 ester | 6.2 | 7.0 |
| Polypropylene containing 40% calcium carbonate dry-blended with 1% isostearate 3.19 ester | 8.5 | 7.2 |
| Polypropylene containing 40% calcium carbonate and 3% isostearate 3.19 ester | 12.2 | Not tested |

The above data clearly show that the addition of the isostearate 3.19 ester of the invention substantially maintains the impact strength of the filled polypropylene in spite of the heat aging, whereas without the isostearate 3.19 ester, the filled polypropylene loses its impact strength (becomes brittle) to a marked degree. The data also show that the impact strength of filled polypropylene is greatly improved by the use of 3% of the isostearate 3.19 ester.

EXAMPLE 17

In this example, the effect of the isostearate 3.19 ester on calcium carbonate-filled polypropylene is evaluated. Two methods are employed to ascertain the effect of the mixing procedures on the physical properties of the end product. In the first method, the calcium carbonate and the organic titanate compound are dry-blended in a Henschel mixer at 3600 rpm for one minute. The mixing takes place initially at room temperature, but the admixture increases in temperature during the mixing operation. Thereafter, test samples are formed by dry-blending with polypropylene, followed by screw injection molding at 450° F. In the second method, the material from the Henschel mixer is compounded in a high shear double concentric screw mixer at 450° F. Thereafter, samples are injection molded at this same temperature. The following table shows the results obtained.

| | Tensile Strength, psi | Flexural Modulus, 10$^3$, psi | Falling Dart Impact, ft.-lbs./in. | Notched Izod ft.-lbs./in. | Unnotched Izod ft.-lbs./in. |
|---|---|---|---|---|---|
| Method 1 | | | | | |
| No Filler | 5,000 | 240 | 1.0 | 0.7 | Not tested |
| 40% CaCO$_3$ No titanate ester | 6,460 | 950 | 0.6 | 0.4 | 2.6 |
| 40% CaCO$_3$ 0.3% titanate ester* | 5,715 | 635 | 1.0 | 0.6 | 3.3 |
| 40% CaCO$_3$ 0.6% titanate ester* | 5,125 | 590 | 1.4 | 1.1 | 6.0 |
| Method 2 | | | | | |
| 40% CaCO$_3$ 0.6% titanate ester* Extruded (high shear mixing) | 4,740 | 460 | 2.5 | 2.0 | 7.4 |

*based on CaCO$_3$

The above table clearly shows that the polypropylene containing the treated calcium carbonate has substantially improved properties, as compared to the untreated filled material. Where 0.6% of the organic titanate is used, the impact strength is markedly improved. Similarly, the use of the double concentric screw used in Method 2 results in a further improvement of properties. It is hypothesized that this additional high shear mixing provides a more thorough reaction between the organic titanate and the inorganic material.

EXAMPLE 18

The application of the invention to polystyrene is shown in this example. The table below shows a comparison of the specific gravity and melt index of polystyrene, polystyrene admixed 50/50 with calcium carbonate, and polystyrene admixed 50/50 with calcium carbonate which has been pretreated with 0.5 part of the isostearate 3.19 ester. The titanate ester and the calcium carbonate were dry-blended in a high shear dry blender initially at ambient conditions. The filler was admixed with the polystyrene in a two-roll mixer at a temperature of 307° F. until mixing was complete. The sheets were comminuted and the specific gravity and melt index determined:

| Material Formulation | Specific Gravity | Melt Index at 190° C., Method E (ASTM) | |
|---|---|---|---|
| | | By Weight in gms. | By Relative Vol. in mls. |
| Unfilled Polystyrene | 1.04 | 0.90 | 0.86 |
| Polystyrene 50% CaCO$_3$ | 1.50 | 0.36 | 0.24 |
| Polystyrene 50% pretreated CaCO$_3$ .5% isostearate 3.19 ester | 1.49 | 1.17 | 0.79 |

The aforesaid table shows that the treated filled polystyrene is more readily moldable. The untreated filled polystyrene has a melt index which indicates that it cannot be as readily molded on conventional equipment.

Having thus described our invention, what we claim and desire to protect by Letters Patent is:

1. A mixture of organo-titanates represented by the formula Ti(OR)$_{4-n}$(OCOR')$_n$ formed by the reaction of a titanate having the formula Ti(OR)$_4$ with $n$ moles of an organic acid having the formula R'COOH, wherein R represents an alkyl group having from 1 to 5 carbon atoms and the organic acid has from 6 to 24 carbon atoms and $n$ is between 3.1 and 3.25.

2. The mixture of organo-titanates of claim 1 wherein the OCOR' group has 18 carbon atoms.

3. The mixture of organo-titanates of claim 1 wherein the OCOR' group is an isostearic group.

4. The mixture of organo-titanates of claim 3 wherein the OR group is an isopropoxy group.

5. A composition of matter comprising a comminuted inorganic material, the surface of which is reacted with a mixture or organo-titanates represented by the formula Ti(OR)$_{4-n}$(OCOR')$_n$ formed by the reaction of a titanate having the formula Ti(OR)$_4$ with $n$ moles of an organic acid having the formula R'COOH, wherein R represents an alkyl group having from 1 to 5 carbon atoms and the organic acid has from 6 to 24 carbon atoms and $n$ is between 3.1 and 3.25.

6. The composition of matter of claim 5 wherein the OCOR' group has 18 carbon atoms and the OR group is an isopropoxy group.

7. The composition of matter of claim 5 wherein the inorganic material is selected from the group consisting of metals, metal oxides, carbon black, sulfur, calcium carbonate, silica, and clay.

8. The composition of matter of claim 7 wherein the metal oxide is zinc oxide, magnesium oxide, titanium oxide, yellow iron oxide, calcium oxide and lead oxide.

9. A process for producing a dispersion of comminuted inorganic material in a polymeric medium which comprises: admixing an inorganic material; an organo-titanate having the formula Ti(OR)$_{4-n}$(OCOR')$_n$ formed by the reaction of a titanate having the formula Ti(OR)$_4$ with $n$ moles of an organic acid having the formula R'COOH, wherein R represents an alkyl group having from 1 to 5 carbon atoms and the organic acid has from 6 to 24 carbon atoms and $n$ is between 3.1 and 3.25; and a polymeric medium; thereby forming a dispersion of the inorganic material, the surface of which has been reacted with the organo-titanate in the polymeric medium.

10. The process of claim 9 wherein the organic titanate is reacted with the surface of said inorganic material prior to admixing with said polymeric medium.

11. The process of claim 9 wherein the organic titanate reacts with the surface of said inorganic material and the polymeric material in situ during the mixing of said three components.

12. A mixture of organo-titanates represented by the formula Ti(OR)$_{4-n}$(OCOR')$_n$ formed by the reaction of tetraisopropyl titanate with $n$ moles of isostearic acid, wherein $n$ is about 3.19.

* * * * *